United States Patent [19]

Eibl et al.

[11] Patent Number: 5,304,383
[45] Date of Patent: Apr. 19, 1994

[54] PHARMACEUTICAL PREPARATION BASED ON LYS-PLASMINOGEN

[75] Inventors: Johann Eibl, Vienna; Anton Philapitsch, Ebenfurt; Hans P. Schwarz, Vienna, all of Austria

[73] Assignee: Immuno Aktiengesellschaft, Vienna, Austria

[21] Appl. No.: 773,103

[22] Filed: Oct. 8, 1991

[30] Foreign Application Priority Data

Oct. 11, 1990 [AT] Austria ................... 2045/90

[51] Int. Cl.$^5$ ............... A61K 9/14; A61K 37/47; A61K 37/02; A61K 37/64
[52] U.S. Cl. ........................... 424/499; 514/8; 514/12; 514/822; 514/922; 530/380; 530/829; 530/381; 530/831; 435/217; 424/94.64
[58] Field of Search ............... 424/499, 94.64; 514/8, 514/12, 21, 822, 922; 530/380, 829, 831, 381; 435/217

[56] References Cited

FOREIGN PATENT DOCUMENTS 0307847 3/1989 European Pat. Off. .
0353218 1/1990 European Pat. Off. .
0474313 1/1992 European Pat. Off. .

OTHER PUBLICATIONS

Whitefleet-Smith, I. et al. "Expression of Human Plasminogen cDNA . . . " Arch. Biochem. Biophys. 271:390–399 (Jun. 1989).
Verstraete et al., "Randomized Trial of Intravenous Recombinant Tissue-Type Plasminogen Activator Versus Intravenous Streptokinase in Acute Myocardial Infarction", The Lancet pp. 842–847 (Apr. 13, 1985).
Lew et al., "The Hypotensive Effect of Intravenous Streptokinase in Patients With Acute Myocardial Infarction", Circulation, 72:1321–1326 (1985).
Vitoux et al., "Treatment of Acute Peripheral Arterial and Graft Thromboses With Intra-Arterial Infusion of Urokinase and Lys–Plasminogen", Trubestein ed., in Konservative Therapie arterieller Durchblutungsstorungen, International Symposium on Conservative Therapy of Arterial Occlusive Diseases, Verlag, Stuttgart pp. 430–432.
Naito, "Study on Thrombolytic Therapy With Lysyl Plasminogen in Patients with Cerebral Thrombosis", Trubestein ed, in Konservative Therapie arterieller Durchblutungsstorungen, International Symposium on Conservative Therapy of Arterial Occlusive Diseases, Verlag, Stuttgart, pp. 343–351.
Rickli and Cuendet, "Isolation of Plasmin-Free Plasminogen with N-terminal Glutamic Acid", Biochem. Biophys. Acta., 250:447–451 (1971).
Markwardt et al., "Fibrinolytika und Antifibrinolytika", VEB Gustav Fischer Verlag, Jena, pp. 95–101, (1972).
Harpel, "Plasma Protease Inhibitors", Proc. Int. Workshop on Protein Separation and Plasma Fractionation, Ed. H. E. Sandberg, pp. 289–302 (1977).

Primary Examiner—Robert A. Wax
Assistant Examiner—Rebecca Prouty
Attorney, Agent, or Firm—Brumbaugh, Graves, Donohue & Raymond

[57] ABSTRACT

There is disclosed a pharmaceutical preparation based on Lys-plasminogen and available in the lyophilized form. This preparation contains a serine-protease inhibitor and optionally an inhibitor co-factor, preferably in an amount of 0.5 to 30 nmol per mg Lys-plasminogen. This preparation is free of side-effects and may be used for the treatment and prophylaxis of plasminogen deficiency syndromes and thromboses as well as for the production of thromboresistant artificial organs.

13 Claims, No Drawings

PHARMACEUTICAL PREPARATION BASED ON LYS-PLASMINOGEN

The invention relates to a pharmaceutical preparation based on Lys-plasminogen from plasma or on recombinantly produced Lys-plasminogen. This preparation according to the invention may be used in the prophylaxis and therapy of thromboses.

It is the goal of every medical treatment of thrombotic conditions to restore vascular integrity by dissolving the thrombus. This may be achieved by the generation of plasmin—and hence of fibrinolytic activity—within the blood and, in particular, at the thrombus site.

The conventional medical treatment consists of infusing into the blood circulation high doses of substances that convert the plasminogen present in the blood to plasmin. (Lancet, 1985 I, pp. 842 to 847). Streptokinase, urokinase, a plasminogen-streptokinase complex and tissue-type plasminogen activator are used as such activators.

A disadvantage inherent in all these activators is that they may result in severe complications in patients, since they act systemically and do not exclusively activate the plasminogen that is adsorbed on the thrombus itself (cf., e.g., Circulation, 1985, Vol. 72, No. 6, pp. 1321 to 1326). This results in the degradation of fibrinogen and coagulation factors and, finally, in hemorrhagic diathesis.

"Lys-plasminogen" is a collective name used in the literature to denote proteolytically modified forms of native plasminogen (=Glu-plasminogen) which are obtained from the latter by cleaving a polypeptide from the NH$_2$-terminus. So far, lysine, methionine and valine have been detected as N-terminal amino acids of the presently known species of Lys-plasminogen. In the literature, values of between 90,000 and 94,000 and values of about 80,000 have been reported as the molecular weights for Glu-plasminogen and Lys-plasminogen, respectively.

Lys-plasminogen has a higher binding affinity to thrombi than Glu-plasminogen. Moreover, it is many times more rapidly activated to plasmin.

There is also described in the literature a treatment consisting of Lys-plasminogen infused either alone or in combination with an activator (e.g., in "Konservative Therapie arterieller Durchblutungsstörungen", G. Trübestein, Bonn, 1986, pp. 343 to 351 and pp. 430 to 432).

All the methods and preparations known today for the treatment or prophylaxis of thromboses and plasminogen deficiency syndromes are unsatisfactory in terms of efficacy. The thrombolytic effect could be increased b the administration of Lys-plasminogen.

Therefore, the invention has as its objective the provision of a pharmaceutical preparation based on Lys-plasminogen which can be administered even in high doses, undesirable side-effects being minimized or avoided. Such side-effects include cardiovascular symptoms such as vasodilatation, drop in blood pressure, increase in respiratory resistance, (bronchoconstriction), influence on heart rate; furthermore, the activation of the endothelium, of the coagulation system, of the thrombocytes, including the kallikrein system leading to thrombin generation. Another side-effect is the release of active thrombin from the thrombus during and after lysis therapy. A further side-effect is the stimulation of the growth of smooth muscle cells of the vessel wall, involving an increased tendency to reocclusion.

The preparation according to the invention is to be present in a lyophilized form and reconstitutable to a solution ready for use.

The pharmaceutical preparation according to the invention based on Lys-plasminogen produced from plasma or based on recombinantly prepared Lys-plasminogen and present in the lyophilized form is characterized by a content of a serine-protease inhibitor optionally of an inhibitor co-factor, more preferably in an amount of from 0.5 to 30 nmol, preferably of from 5 to 25 nmol, per mg of Lys-plasminogen. The invention is based on the finding that the application of Lys-plasminogen does not involve any of the side-effects pointed out above if administered commonly with an inhibitor and, optionally with an inhibitor co-factor in the amounts indicated above.

Preferred embodiments of the preparation according to the invention contain aprotinin, antithrombin III, $a_1$-antitrypsin, $a_2$-macroglobulin or $C_1$-esterase inhibitor as serine-protease inhibitors.

Another preferred embodiment has proved to be the combination of antithrombin III as the serine-protease inhibitor and an inhibitor co-factor, preferably heparin.

The ready-to-use solution of the preparation according to the invention advantageously contains Lys-plasminogen at a concentration of 1 to 50 mg, preferably 2.5 mg to 25 mg, per ml of the ready-for-use solution.

The invention also covers the use of Lys-plasminogen in combination with a serine-protease inhibitor for producing preparations for the treatment or prophylaxis of plasminogen deficiencies and thromboses and for producing thrombosis resistant artificial organs.

The plasminogen present in the preparation according to the invention also exhibits better adsorption on blood vessels and artificial surfaces, as will be explained further below.

The invention will be explained in more detail by means of the following examples.

1. Preparation of a Lys-Plasminogen Solution

Preparation 1

1 kg Cohn III precipitate was suspended at 0° C. in 10 l of a phosphate buffer previously admixed with 10 KIU/ml aprotinin (1 KIU corresponding to 0.022 nmol). After precipitation with ethanol (10%, −2° C.) it was centrifuged and the supernatant was filtered over a deep-bed filter based on cellulose (AMF Cuno Zeta Plus 50 S). Subsequently, it was diluted with 5 l phosphate buffer and 500 g lysine polyacrylamide gel (prepared according to E. E. Rickli and P. A. Cuendet, Biochem. Biophys. Acta 250, 447–451 (1971)) were stirred in. After stirring for one hour at 0° C., the gel loaded with plasminogen was separated by filtration over Büchner funnels and washed with phosphate buffer until no protein was detectable in the filtrate any longer. By stirring with a solution of 6-aminocaproic acid (0.1 mol/l) in phosphate buffer, plasminogen was eluted and precipitated by the addition of ammonium sulfate (261 g per kg eluate).

The precipitate recovered by centrifugation was dissolved in an isotonic phosphate/saline buffer and dialyzed for 36 hours at a temperature of 5° C.; the preparation contained 15 mg plasminogen per ml; a content of "Lys-plasminogen" of 98% was detected by SDS-PAGE.

Preparation 2

The extraction of Cohn III precipitate with phosphate buffer was carried out after the addition of 2 KIU/ml aprotinin; precipitation with ethanol, centrifugation and filtration were effected in a manner analogous to preparation 1. After dilution with phosphate buffer, the solution was pumped over a column packed with lysine polyacrylamide gel. Washing and elution were effected by means of the solutions described above, but within the column. Upon precipitation with ammonium sulfate, centrifugation and dissolution of the precipitate in a manner analogous to preparation 1, dialysis was carried out for 40 hours at a temperature of 7° C.; the preparation contained 15 mg plasminogen per ml; a content of "Lys-plasminogen" of 93% was detected by means of SDS-PAGE.

2. Influence of Aprotinin on Side-Effects of Spontaneous Lysis (in vivo)

A Lys-plasminogen preparation having a content of 500 CU (33 mg) was produced as described above and admixed with 9 mg NaCl and with 5000 (110 nmol) units of aprotinin (1 KIU corresponding to 0.022 nmol; F. Markwardt, H. Landmann and H. P. Klöcking in "Fibrinolytika und Antifibrinolytika", VEB Gustav Fischer Verlag, Jena (1972), pp. 95-101) (the amounts indicated being based on 1 ml ready-for-use solution). This corresponds to 3.3 nmol inhibitor per mg Lys-plasminogen. The mixture remained at room temperature for one hour. The above Lys-plasminogen preparation was intravenously administered as a bolus of 2 ml per kg to narcotized rabbit, resulting in 1000 units of Lys-plasminogen (66 mg) and 10,000 units of aprotinin per kg body weight. Blood samples were drawn before the administration of the preparation, and 30 min, 1 hr, 2 hrs, 3 hrs, 4 hrs, 5 hrs following administration. The number of thrombocytes in the blood was measured by means of the Coulter counter (Coulter Electronics GmbH, Krefeld). For comparison, the same amount of Lys-plasminogen without addition of aprotinin was injected in parallel assays. The results are summarized in the following Table 1.

TABLE 1

| | Thrombocyte number G/l | |
|---|---|---|
| | Lys-plasminogen without aprotinin | Lys-plasminogen with aprotinin |
| prior to appl. | 366 | 395 |
| 30 min after appl. | 238 | 422 |
| 1 hr after appl. | 174 | 369 |
| 2 hrs after appl. | 285 | 367 |
| 3 hrs after appl. | 245 | 342 |
| 4 hrs after appl. | 304 | 360 |
| 5 hrs after appl. | 325 | 376 |

As can be seen, the thrombocytes were reduced by 52% during the spontaneously occurring fibrinolytic process after application of plasminogen. This undesired side-effect of the thrombolytic process was avoided by the combination of plasminogen and aprotinin.

3. Influence of Antithrombin III/Heparin on Side-Effects of Spontaneous Lysis (in vivo)

A Lys-plasminogen preparation comprising 33 mg (500 CU) plasminogen was admixed with 9 mg NaCl and with a mixture of antithrombin III and heparin (1:6) such that 25 U antithrombin III (115 nmol) and 150 U heparin additionally resulted per ml solution. This corresponds to 3.5 nmol antithrombin III per mg Lys-plasminogen. 2 ml/kg body weight of this mixture of active substance and inhibitors were administered to a narcotized rabbit. Blood was taken at predetermined intervals before and after the administration of Lys-plasminogen and of the inhibitors, and the thrombocytes were counted in the Coulter counter. Likewise, the plasminogen level was amidolytically determined from plasma. The determination was performed by mean of chromogenic plasmin substrate S 2251 from Kabi. In a manner known per se, Lys-plasminogen was cleaved to Lys-plasmin by means of an excess of activators and the amidolytic activity of Lys-plasmin was measured via the release of the colorant p-nitroaniline in a tris buffer medium (pH 7.4). From these values, the half-life of the infused Lys-plasminogen was determined by means of regression calculation. A parallal assay without addition of inhibitor was run for comparison. The results are summarized in Table 2.

TABLE 2

| | Lys-plasminogen without inhibitor | | Lys-plasminogen with AT III/heparin | |
|---|---|---|---|---|
| | Thrombocytes G/l | Plasminogen CU/ml | Thrombocytes G/l | Plasminogen CU/ml |
| bef. appl. | 366 | 0.02 | 233 | 0.06 |
| 30 min after appl. | 238 | 18 | 220 | 6.4 |
| 1 hr after appl. | 174 | 11.5 | 242 | 6.4 |
| 2 hrs after appl. | 285 | 11 | 209 | 4.8 |
| 3 hrs after appl. | 245 | 7 | 238 | 5.2 |
| 4 hrs. after appl. | 304 | — | 211 | 3.8 |
| 5 hrs. after appl. | 325 | 5 | 202 | 3.6 |
| Half-life | | 129 min | | 296 min |

As is apparent, the rabbits treated with Lys-plasminogen and antithrombin III/heparin demonstrated that, on the one hand, the spontaneous decrease of thrombocytes as a side-effect of thrombolysis was avoided and, on the other hand, the half-life of Lys-plasminogen in the plasminogen-inhibitor mixture was prolonged.

4. Influence of $C_1$-Inhibitor on Side-Effects of Spontaneous Lysis (in vivo)

A Lys-plasminogen preparation containing per ml 500 CU (=33 mg) Lys-plasminogen and 9 mg NaCl was admixed with 125 U (=212 nmol) $C_1$-inhibitor. This corresponds to 6.4 nmol $C_1$-inhibitor per mg Lys-plasminogen (1 U corresponding to 1.7 nmol; P. C. Harpel in: "Proc. Int. Workshop on Protein Separation and Plasma Fractionation"; Ed. H. E. Sandberg (1977); pp. 289-302). 2 ml of the above solution were intravenously injected in a narcotized rabbit. Blood was taken before and after the application. A Lys-plasminogen preparation without addition of inhibitor served for comparison. The coagulability of the whole blood was measured by means of a thromboelastograph (manufacturer: Hellige). The reaction time until clot formation after the addition of $CaCl_2$ to citrate-stabilized whole blood was measured in vitro. The results are summarized in Table 3.

TABLE 3

| | Coagulation time in min | |
|---|---|---|
| | Lys-plasminogen without inhibitor | Lys-plasminogen + $C_1$-inhibitor |
| before appl. | 18 | 15 |
| 1 hr after appl. | 21 | 16 |
| 2 hrs after appl. | | 12 |
| 3 hrs after appl. | no clotting | 13 |
| 4 hrs after appl. | >60 min | 12 |
| 5 hrs after appl. | | 10 |

The activation of the fibrinolytic system constitutes a high degree of strain on the body. In the extreme case, severe hemorrhagic complications may occur due to the incoagulability of the blood. This was revealed when administering Lys-plasminogen without inhibitors. However, if Lys-plasminogen with $C_1$-inhibitor is injected, incidents, such as hemorrhagic complications, will be avoided.

5a. Influence on Respiratory Pressure in Guinea-Pigs

If 66 mg (1000 U) Lys-plasminogen/kg are intravenously administered to a narcotized guinea-pig and thrombolysis therapy is initiated after one hour by applying 200,000 units urokinase (UK) per kg body weight, a spontaneous increase in the respiratory pressure upon UK administration is revealed. However, if Lys-plasminogen is pre-mixed with $\alpha_2$-macroglobulin and applied at a ratio of 230 mg $\alpha_2$-macroglobulin (=317 nmol) and 1000 units (66 mg) Lys-plasminogen per kg body weight (corresponding to 4.8 nmol $\alpha_2$-macroglobulin per mg Lys-plasminogen), and if the therapy is started after 60 min of latency likewise with 200,000 units UK/kg, no increase in the respiratory pressure takes place after application of UK.

TABLE 4

| | Respiratory pressure (in % of initial value) | | |
|---|---|---|---|
| | Before appln. of UK | After appln. of UK | Variation coefficient |
| Lys-plasminogen | 100% | 140% (rel.) | 10% |
| Lys-plasminogen + $\alpha_2$M | 100% | 93% (rel.) | 20% |

5b. Influence on Blood Pressure in Guinea-Pigs

Similarly, undesired side-reactions were observed in the spontaneous drop in blood pressure. As described above, the blood pressure was monitored during the thrombolysis therapy with urokinase and Lys-plasminogen in the guinea-pig model.

At an application of 1000 units (66 mg) Lys-plasminogen/kg, no significant changes in blood pressure were registered. After the application of 200,000 UK/kg, a spontaneous drop occurred, lasting till the end of the assay (about 20 min). No recovery phase was observed. However, when Lys-plasminogen was pre-mixed with $C_1$-inhibitor and this mixture of 1000 units Lys-plasminogen (66 mg) and of 1000 units $C_1$-inhibitor (1700 nmol) per kg was applied (which corresponds to 25 nmol $C_1$-inhibitor per mg Lys-plasminogen) followed by UK administration, a slight drop in blood pressure occurred, yet regaining the initial value after 5 minutes, and thus normalizing.

5c. Influence on Respiratory Pressure in Guinea-Pigs

In the same animal model, the combination of Lys-plasminogen [$\alpha_2$-macroglobulin] $C_1$-inhibitor was tested. 230 mg $\alpha_2$-macroglobulin were pre-mixed with 1000 units $C_1$-inhibitor and 1000 units (66 mg) Lys-plasminogen, which mixture was injected per kg guinea-pig. No increase in the respiratory pressure occurred after UK administration at 200,000 units/kg.

6. Adsorption of Lys-Plasminogen a) Adsorption on blood vessels

A Lys-plasminogen solution having an inhibitor content (aprotinin, $C_1$-esterase inhibitor) of 0.6 nmol/mg plasminogen was tested on a rabbit aorta for its adsoroption behavior. Native Glu-plasminogen without any inhibitor added served for comparison.

An aorta was taken from a sacrificed rabbit and invertedly drawn on glass rods in pieces. (Lys- and Glu-) plasminogen solutions were prepared in a tyrode solution and the aortas having surfaces of approximately 1 $cm^2$ were incubated with 0.5 ml plasminogen solution at a concentration of 0.015 mg plasminogen per ml at 37° C. for 10 min, 30 min and 60 min. After the contact time, the aorta pieces were removed from the plasminogen solutions and washed with tyrode solution. The aortas adsorbed with plasminogen were put into a vessel containing 500 $\mu$l tyrode solution, 50 $\mu$l urokinase (by Medac) at 25,000 IU/ml, 50 $\mu$l chromogenic substrate S 2251 (by Kabi). Incubation took place at 37° C. for 10 min. Plasminogen adsorbed on the aorta was converted into Lys-plasmin by means of UK. The splitting rates at which Lys-plasmin splits off the chromogenic substrate P-nitroaniline was measured photometrically after the reactions had been stopped by means of 400 $\mu$l acetic acid.

TABLE 5

| | $nmol/min.cm^2$ | |
|---|---|---|
| | Lys-plasminogen (incl. inhibitor) | Glu-plasminogen (native) |
| Contact time Plasminogen - aorta | | |
| 10 min | 0.56 | 0.03 |
| 30 min | 1.2 | 0.2 |
| 60 min | 2.1 | 0.16 |

The Lys-plasminogen preparation adsorbs on the blood vessel to a much greater extent and can be converted to plasmin by an activator, the inhibitors contained in the preparation prevent neither adsorption nor activation.

b) Adsorption on artificial surfaces

Lys-plasminogen having an inhibitor content of 0.6 nmol/mg plasminogen is tested on artificial surfaces for its adsorption behavior. A naturally available Glu-plasminogen without any inhibitors added serves for comparison.

Both Lys-plasminogen and Glu-plasminogen are adjusted to a concentration of 4 mg plasminogen per ml in physiologic NaCl solutions. 250 $\mu$l of the sample are pipetted into wells. Plastic combs are suspended in the filled wells (Polystyrol 158K by BASF), the adsorption of plasminogen taking place on the surfaces of the same. After 60 min, 120 min contact time at room temperature, the plastic platelets are removed, washed and placed into a reaction mixture including 100 $\mu$l tris buffer, pH 7.2, 50 $\mu$l urokinase (by Medac) 25,000 IU/ml and 50 $\mu$l chromogenic substrate S 2251 (by Kabi). After 10 min at room temperature, 50 $\mu$l acetic acid is added and the reaction is stopped. With UK, the adsorbed plasminogen is converted to plasmin, which cleaves the chromogenic substrate. The reaction of the chromogenic substrate allows the inference that adsorption on artificial surfaces takes place.

TABLE 6

| | nmol/min.cm² | |
|---|---|---|
| | Lys-plasminogen (incl. inhibitor) | Glu-plasminogen (native) |
| Contact time | | |
| 60 min | 0.23 | 0.09 |
| 120 min | 1.2 | 0.19 |

Again, it is apparent that Lys-plasminogen including inhibitors is adsorbed in a clearly better and faster way than Glu-plasminogen without inhibitors, and also is activatable without influence of the inhibitors contained in the preparation.

7. Production of the Pharmaceutical Preparation According to the Invention

In the following, the production of two pharmaceutical preparations according to the invention is described, starting from the dialysates obtained in preparation 1 and preparation 2. The two preparations differ with regard to their contents of inhibitors.

a) 32 ml of the dialysate of Lys-plasminogen preparation 1 having a content of 15 mg Lys-plasminogen per ml were admixed with 6.4 ml of a $C_1$-esterase inhibitor preparation ($C_1$-esterase inhibitor STIM 3 Human Haemoderivate 500 units per 10 ml). Subsequently, 20 mg aprotinin were added, resulting in a concentration of 10 units (=17 nmol) $C_1$-esterase inhibitor and 4469 KIU (=98 nmol) aprotinin per ml Lys-plasminogen solution with 15 mg Lys-plasminogen. From this, an inhibitor content of 7.7 nmol per mg Lys-plasminogen is calculated. The solution remained at 4° C. for at least 15 min, was admixed with 20 mmol lysine per liter, adjusted to a pH of 7, lyophilized, heat-treated for virus inactivation, dissolved, sterile-filtered, filled and lyophilized in final containers.

b) 32 ml of the dialysate of Lys-plasminogen preparation 2 having a content of 15 mg Lys-plasminogen per ml were admixed with 1280 ml of a $C_1$-esterase inhibitor preparation (see above) and 1.79 mg aprotinin and processed as described above. With this preparation, an inhibitor content of 0.81 nmol per mg Lys-plasminogen resulted.

8. Applications

Persons suffering from conditions caused by congenital plasminogen deficiency characterized both by quantitative and qualitative defects have an increased risk of developing thrombotic conditions. Frequently, thrombotic incidents are provoked by external circumstances such as traumas, surgery, pregnancy, infections, inflammatory processes.

For treatment and prophylaxis in these plasminogen-deficient patients, Lys-plasminogen may be infused in doses of from 10 to 100 U/kg 2 to 4 times a day. Lys-plasminogen, either alone or in combination with an activator, also may be used in the prophylaxis and therapy of a number of acquired diseases such as disseminated intravascular coagulation, peripheral arterial thrombosis, intracardial thrombosis, insult, myocardial infarction. Today, systemic or local (intracoronary) thrombolysis by means of urokinase, streptokinase, or tissue-plasminogen activator has become established in the therapy of myocardial infarction.

However, the success of the rate of lysis depends on the age of the thrombus, and in many cases coronary thrombi remain lysis-resistant due to late hospitalization. By the application of the preparation according to the invention either systemically or locally (even in body cavities), it is possible to effect the enrichment of Lys-plasminogen at the thrombus and, therefore, increase the rate of lysis of the subsequent activator-proactivator application.

The preparation according to the invention may be applied intravenously, subcutaneously or perorally immediately upon commencement of clinical symptoms or in case of a suspected myocardial infarction prior to confirmation of the diagnosis and build up in the developing thrombus. Thus, the time interval during which effective thrombolysis is achieved by fibrinolytically effective activators is increased.

A frequent problem in thrombolysis is the reocclusion of the vessel after it has been successfully opened. Local or systemic application after thrombolysis can result in a film-like coating of the damaged or arteriosclerotically changed vessel surface with Lys-plasminogen, thus preventing reocclusion by the thrombosis resistant surface obtained.

The restenosis observed after angioplastic operations is prevented by application of the preparation according to the invention prior, during and after angioplastics.

Deep venous thrombosis of the leg which is resistant to conventional therapies, may be successfully treated by application distally from the thrombosis simultaneously with systemic lysis therapy.

The production of thrombosis resistant vascular prostheses is effected by coating the surface with Lys-plasminogen; likewise, Lys-plasminogen is suitable for the production of artificial thromboresistant organs, e.g., cardiac valves, artificial joints. Lys-plasminogen can be mixed with proenzymes and/or enzymes. These preparations produced in vitro develop their thrombolytic activities upon application in vivo.

The Lys-plasminogen administered with the preparation according to the invention with subsequent activator treatment (e.g., urokinase) reduces the risk of reocclusion.

Patients suffering from impaired lipid metabolism, in particular those having elevated Lp(a), are characterized by severe atherosclerosis caused by a defective resorption behavior of their vessel walls. Due to its structural similarity to Lp(a), substitution with Lys-plasminogen in such patients prevents the uptake of Lp(a) into the vessel wall, attenuates the atherosclerotic process and renders it reversible.

What we claim is:

1. A pharmaceutical preparation comprising Lys-plasminogen and a serine protease inhibitor in an amount of from 0.5 to 30 nmol of the inhibitor per mg Lys-plasminogen.

2. The pharmaceutical preparation according to claim 1, wherein the Lys-plasminogen is recovered from plasma.

3. The pharmaceutical preparation according to claim 1, wherein the Lys-plasminogen is recombinantly produced Lys-plasminogen.

4. The pharmaceutical preparation according to claim 1, wherein the serine protease inhibitor is in an amount of from 5 to 25 nmol per mg Lys-plasminogen.

5. The pharmaceutical preparation according to claim 1, further comprising an inhibitor co-factor.

6. The pharmaceutical preparation according to claim 1, wherein the serine protease inhibitor is selected from the group consisting of aprotinin, $\alpha_2$-macroglobulin, $\alpha_1$-antitrypsin, antithrombin III and $C_1$-esterase inhibitor of human, animal or recombinant origin.

7. The pharmaceutical preparation according to claim 6, wherein the serine protease inhibitor is antithrombin III.

8. The pharmaceutical preparation according to claim 5, further comprising heparin as inhibitor co-factor.

9. The pharmaceutical preparation according to claim 1, wherein the inhibitor and Lys-plasminogen are lyophilized.

10. The pharmaceutical preparation according to claim 9, wherein the lyophilized inhibitor and Lys-plasminogen are reconstitutable to a ready-for-use solution having Lys-plasminogen at a concentration of 1 mg to 50 mg per ml of said ready-for-use solution.

11. The pharmaceutical preparation according to claim 10, wherein the Lys-plasminogen is present at a concentration of from 2.5 mg to 25 mg per ml of said ready-for-use solution.

12. A method of treating and preventing plasminogen deficiency and thrombosis in a patient comprising the administration of an effective amount of Lys-plasminogen in combination with a serine-protease inhibitor wherein the serine-protease inhibitor is present in an amount of from 0.5 to 30 nmole of the inhibitor per mg Lys-plasminogen.

13. A method of treating a patient suffering from thrombosis comprising the administration of an effective amount of Lys-plasminogen in combination with a serine-protease inhibitor wherein the serine-protease inhibitor is present in an amount of from 0.5 to 30 nmole of the inhibitor per mg Lys-plasminogen.

* * * * *